United States Patent

Sasaoka et al.

Patent Number: 5,919,924
Date of Patent: Jul. 6, 1999

[54] PROCESS FOR PREPARING 3-HALOGENATED CEPHEM DERIVATIVE

[75] Inventors: Michio Sasaoka, Tokushima; Shigeru Torii, Oakayama-ken; Hideo Tanaka, Okayama; Ryo Kikuchi, Tokushima; Yutaka Kameyama, Tokushima; Kouichi Sorajo, Tokushima, all of Japan

[73] Assignee: Otsuka Kagaku Kabushiki Kaisha, Osaka, Japan

[21] Appl. No.: 08/849,393

[22] PCT Filed: Nov. 8, 1996

[86] PCT No.: PCT/JP96/03298

§ 371 Date: Jun. 3, 1997

§ 102(e) Date: Jun. 3, 1997

[87] PCT Pub. No.: WO97/17353

PCT Pub. Date: May 5, 1997

[30] Foreign Application Priority Data

Nov. 10, 1995 [JP] Japan .................... 7-317255

[51] Int. Cl.⁶ .................................. C07D 501/59
[52] U.S. Cl. ........................................ 540/215
[58] Field of Search ............................. 540/215

[56] References Cited

FOREIGN PATENT DOCUMENTS 4-282387  10/1992  Japan .

OTHER PUBLICATIONS

Tanaka et al, Bull. Chem. Soc. Japan, (1996) vol. 69, No. 5 pp. 1391–1396.
Tanaka et al, Synlett (1991) No. 12, pp. 888–890.

Primary Examiner—John M. Ford
Attorney, Agent, or Firm—Kubovcik & Kubovcik

[57] ABSTRACT

A process for preparing a 3-halogenated cephem derivative represented by the formula (2), characterized by causing a halogenating reagent to act on an allenyl β-lactam compound represented by the formula (1) in the presence of a cuprous salt or cupric salt to obtain the 3-halogenated cephem derivative

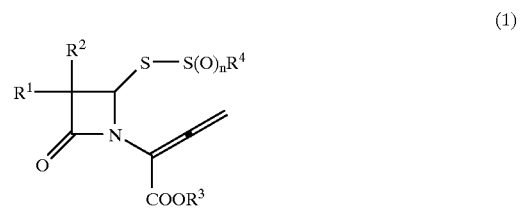

(1)

wherein $R^1$ is a hydrogen atom, amino or protected amino, $R^2$ is a hydrogen atom, halogen atom, lower alkoxyl, lower acyl, lower alkyl, lower alkyl having at least one selected from hydroxyl and protected hydroxyl as a substituent, hydroxyl or protected hydroxyl, $R^3$ is a hydrogen atom or carboxylic acid protecting group, $R^4$ is an aromatic compound residue which may have a substituent or nitrogen-containing aromatic heterocyclic compound residue which may have a substituent, and n is 0 to 2

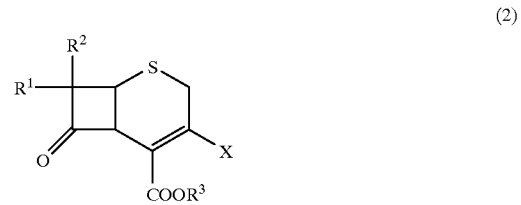

(2)

wherein $R^1$, $R^2$ and $R^3$ are as defined above, X is a halogen atom.

10 Claims, No Drawings

PROCESS FOR PREPARING 3-HALOGENATED CEPHEM DERIVATIVE

TECHNICAL FIELD

The present invention relates to a process for preparing 3-halogenated cephem derivatives.

The 3-halogenated cephem derivative is useful as an intermediate for giving known cephem antibiotics which are administered mainly orally and is converted to cefaclor according to a later-mentioned Reference Example 1 (JP-A-39313/1986).

BACKGROUND ART

Reports have been made on widely acceptable processes for preparing 3-halogenated cephem derivatives represented by the formula (2). These processes include a process which uses a compound of the formula (3), i.e., 3-hydroxycephem compound and involves the conversion of hydroxyl group to trifluoromesyloxy group first and the subsequent reaction with a lithium halide [J. Org. Chem., 54, 4962(1989)], and a process wherein a reactive chlorine or bromine compound (such as phosphorus trichloride, phosphorus oxychloride or thionyl bromide) is reacted with a 3-hydroxycephem compound in dimethylformamide (JP-A-116095/1974).

(3)

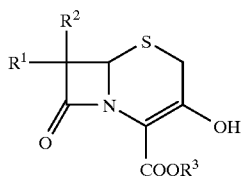

wherein $R^1$, $R^2$ and $R^3$ are as defined below.

These processes requires the use of the 3-hydroxycephem compound as the starting material which compound itself is difficult to prepare, so that the process is in no way industrially feasible.

Further, a process is known wherein an allenyl β-lactam compound of the formula (1) is reacted with a halogen salt of alkali metal or alkaline earth metal to cyclize the allenyl β-lactam compound to obtain the 3-halogenated cephem compound (JP-A-282387/1992). This process is advantageous in employing the starting material, allenyl β-lactam compound, which is easily available, but inevitably forms 3-sulfonylcephem as a by-product due to the recombination of sulfinate ion which is released on ring closure, consequently giving the desired 3-halogenated cephem derivative in a yield of as low as up to 70%.

An object of the present invention is to provide a process for preparing the desired 3-halogenated cephem derivative in a high yield with a high purity by a safe and simplified procedure without using a starting material which is difficult to prepare.

DISCLOSURE OF THE INVENTION

The present invention provides a process for preparing a 3-halogenated cephem derivative represented by the formula (2), characterized by causing a halogenating reagent to act on an allenyl β-lactam compound represented by the formula (1) in the presence of a cuprous salt or cupric salt to obtain the 3-halogenated cephem derivative (1)

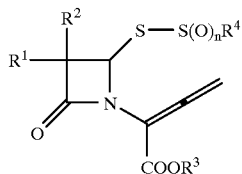

wherein $R^1$ is a hydrogen atom, amino or protected amino, $R^2$ is a hydrogen atom, halogen atom, lower alkoxyl, lower acyl, lower alkyl, lower alkyl having at least one selected from hydroxyl and protected hydroxyl as a substituent, hydroxyl or protected hydroxyl, $R^3$ is a hydrogen atom or carboxylic acid protecting group, $R^4$ is an aromatic compound residue which may have a substituent or nitrogen-containing aromatic heterocyclic compound residue which may have a substituent, and n is 0 to 2

(2)

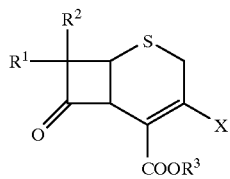

wherein $R^1$, $R^2$ and $R^3$ are as defined above, X is a halogen atom.

In the investigation of a widely useful process for preparing 3-halogenated cephem derivatives, we directed attention to the process disclosed in the aforementioned publication JP-A-282387/1992, and continued the investigation under an anticipation of making possible to restrict formation of by-products by converting the sulfinate ion to less-nucleophilic group. As a result, we have found that the sulfinate ion is oxidized to less-nucleophilic sulfonic acid group by conducting a specific oxidation together with the ring closure to obtain the desired 3-halogenated cephem derivative in a high yield.

Namely, we made an intensive investigation on various oxidation reactions, and found an entirely novel fact that use of a hologenating agent in combination with the oxidation reaction using cuprous salt or cupric salt at the same time affords the desired 3-halogenated cephem derivative quantitatively.

Examples of groups mentioned herein are as follows. Examples of halogen atom are fluorine, chlorine, bromine or iodine atom. Exemplary of the lower alkyl are straight-chain or branched $C_{1-4}$ alkyl group such as methyl, ethyl, n-propyl, isopropyl, n-butyl, isobutyl, sec-butyl or tert-butyl. Exemplary of aryl are phenyl and naphthyl.

Exemplary of the protected amino represented by $R^1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218–287). Examples of protective groups for the amino of phenylglycylamido group and p-hydroxyphenylglycylamido group are those disclosed in the literature, Chap. 7 (pp. 218–287). Examples of protective groups for the hydroxyl of p-hydroxyphenylglycylamido group are those disclosed in the literature, Chap.2 (pp. 10–72).

Further, also are included groups of the formula (5)

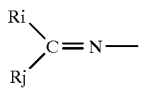

(5)

wherein Ri and Rj are same or different and each a hydrogen atom, aliphatic hydrocarbon group, aromatic hydrocarbon group or heterocyclic hydrocarbon group, or may bond together to form a cyclic group.

Exemplary of the lower alkoxyl represented by $R^2$ are straight-chain or branched $C_{1-4}$ alkoxyl groups such as methoxy, ethoxy, n-propoxy, isopropoxy, n-butoxy, isobutoxy, sec-butoxy and tert-butoxy groups.

Exemplary of the lower acyl represented by $R^2$ are straight-chain or branched $C_{1-4}$ acyl groups such as formyl, acetyl, propionyl, butyryl and isobutyryl.

Examples of protective groups for the protected hydroxyl in the lower alkyl represented by $R^2$ and substituted with at least one selected from hydroxyl and protected hydroxyl, and for the protected hydroxyl represented by $R^2$ are those disclosed in the literature, Chap. 2 (pp. 10–72). The substituted lower alkyl represented by $R^2$ may have as its substituent(s) one or at least two same or different groups selected from among hydroxyl and the protected hydroxyl groups. Such substituent(s) may be positioned on at least one carbon atom of the alkyl.

Exemplary of the carboxylic acid protecting group represented by $R^3$ are allyl, benzyl, p-methoxybenzyl, p-nitrobenzyl, diphenylmethyl, trichloromethyl, tert-butyl, and those disclosed in the literature, Chap. 5 (pp. 152–192).

Examples of aromatic residue, substituted aromatic residue, nitrogen-containing aromatic residue and substituted nitrogen-containing aromatic residue represented by $R^4$ are phenyl, naphthyl, benzothiazol, triazol, thiazol, tetrazol group, etc. Exemplary of the substituent which may be substituted in these groups are halogen atoms (such as fluorine, chlorine, bromine, iodine atom), straight-chain or branched $C_{1-4}$ alkoxyl groups (such as methoxy, ethoxy), straight-chain or branched $C_{1-4}$ alkylthio groups (such as methylthio, ethylthio), straight-chain or branched $C_{1-4}$ alkylsulfonyloxy groups (such as methanesulfonyloxy, trifluoromethanesulfonyloxy), aromatic sulfonyloxy or substituted aromatic sulfonyloxy (such as benzenesulfonyloxy, toluenesulfonyloxy), straight-chain or branched $C_{1-4}$ alkyl groups (such as methyl, ethyl), amino, amino which has as a substituent one or two straight-chain or branched $C_{1-4}$ alkyl groups (such as methylamino, dimethylamino, ethylamino, diethylamino), hydroxyl, acyloxy group represented by R'COO— wherein R' is phenyl, tolyl, or straight-chain or branched $C_{1-4}$ alkyl group (such as phenylcarbonyloxy, acetyloxy), acyl group represented by R'CO— wherein R' is as defined above (such as phenylcarbonyl, acetyl), nitro, cyano, phenyl, etc. When the residue is phenyl group, the phenyl may have 1 to 5, especially 1 to 3, same or different groups selected from among the above substituents. When the residue is naphthyl group, the naphthyl may have 1 to 7, especially 1 to 3, same or different groups selected from among the above substituents.

Examples of halogen atom represented by X are fluorine, chlorine, bromine or iodine atom and among which especially preferable are chlorine, bromine and iodine atom.

The allenyl β-lactam compound represented by the formula (1) and serving as a starting material of the invention can be prepared, for example, by reacting a β-lactam compound represented by the formula (4) and a base in a solvent according to a method disclosed in JP-A-282,359/1992

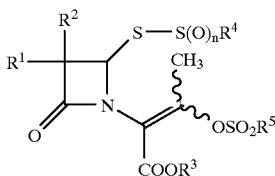

(4)

wherein $R^1$, $R^2$, $R^3$, $R^4$ and n are as defined above, $R^5$ is lower alkyl which may have a substituent or aryl which may have a substituent.

The solvent is not specifically limited so far as it does not cause an adverse effect. Examples of solvents are alcohols such as methanol, ethanol, propanol, isopropanol, butanol and tert-butanol, lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, dimethylsulfoxide, etc. These solvents are used singly or in admixture of at least two of them. These solvents may contain water as required. These solvents are used in an amount of about 10 to about 200 liters, preferably about 20 to about 100 liters, per kilogram of the β-lactam compound of the formula (4).

It is possible to use a base which is known in the art. Examples of useful bases are N,N,N-tri lower alkyl amines such as trimethylamine, dimethylethylamine, triethylamine and diisopropylethylamine, N-lower alkyl azacycloalkanes such as N-methylpiperidine and N-ethylpiperidine, N-phenyl lower alkyl-N,N-di lower alkyl amines such as N-benzyl-N,N-dimethylamine and N-benzyl-N,N-diethylamine, N,N-dialkyl aromatic amines such as N,N-dimethylaniline, nitrogen-containing aromatic amines such as pyridine, bicycloamines such as diazabicycloundecene and diazabicyclononene, and a mixture of these amines. These bases are used usually in an amount of 1 to 10 equivalents based on the β-lactam compound of the formula (4). When required, it is recommended the base is added until the β-lactam compound of the formula (4) is consumed.

The reaction is conducted usually at −78° C. to +60° C., preferably −40° C. to +30° C.

The resulting allenyl β-lactam compound of the formula (1) can be isolated by the usual purification method but can be used in the next reaction without purification.

In the present invention, the ring closure occurs at the same time of halogen substitution at an allenyl group of the allenyl β-lactam compound of the formula (1) by causing a halogenating reagent to act on the allenyl β-lactam compound in the presence of a cuprous salt or cupric salt, and thereby released sulfinate ion is oxidized by the catalyst copper salt to sulfonic acid group and the recombination of the sulfinate ions is prevented.

The cuprous salt and cupric salt are not specifically limited and include halogenated copper salts such as cuprous chloride (I), cupric chloride (II), cuprous bromide (I), cupric bromide (II), cuprous iodide (I), cupric iodide (II), cuprous fluoride (I) and cupric fluoride (II); strong acid copper salts such as cupric sulfate (I), cupric nitrate (II) and cupric perchlorate (II); copper oxides such as cuprous oxide (I) and cupric oxide (II); organic metal copper complex such as copper acetylacetonate. Halogenated copper salt is preferable as cuprous salt and halogenated copper salt and strong acid copper salt are preferable as cupric salt. Among these copper salts particularly preferable are cuprous chloride (I), cupric chloride (II), cupric sulfate (II) and cupric perchlorate (II). The copper salt may be anhydrous or may contain crystal water. The copper salt is used singly or in admixture of at least two of them. The copper salt is used in an amount of about 0.005 to about 10 equivalents, preferably about 0.05 to about 2 equivalents per equivalent of the allenyl β-lactam compound of the formula (1), although not limited specifically, varies widely and is suitably selected depending on the kind of the copper salt, the amount of the allenyl β-lactam compound of the formula (1), halogenating reagent, and reaction conditions.

Conventional halogenating reagents can be used and examples thereof are metal halides and quaternary ammonium halides. The metal halides include aluminum halides such as aluminum chloride and aluminum bromide; silyl halide derivatives such as trimethylsilyl chloride; alkali metal halides such as lithium chloride, lithium bromide and lithium iodide; alkaline earth metal halides such as calcium chloride, calcium bromide, calcium iodide, barium chloride, barium bromide, barium iodide, strontium chloride, strontium bromide and strontium iodide; rare earth metal halides such as cerium chloride; and other various metal halides. The quaternary ammonium halides include ammonium chloride, triethylamine hydrochloride, tetra-n-butylammonium chloride, triethylbenzylammonium bromide and tetrabenzylammonium chloride.

Preferable halogenating reagents are those shown by the formula below (M)mX or $(R^6)(R^7)(R^8)(R^9)N\ X$ wherein m is an integer of 1 to 3, M is alkali metal, alkaline earth metal, aluminum or trialkylsilyl, $R^6$ to $R^1$ are the same or different and are hydrogen atom, alkyl, aryl or aralkyl. In case when m is 1, M is alkali metal such as lithium and sodium, or trialkylsilyl such as trimethylsilyl. In case when m is 2, M is alkaline earth metal such as magnesium and calcium. In case when m is 3, M is aluminum or the like. In $R^6$ to $R^9$, examples of alkyl are those having 1 to 4 carbon atoms as mentioned above, examples of aryl are phenyl and naphthyl, examples of aralkyl are benzyl and phenethyl. The halogenating reagent is used singly or in admixture of at least two of them. The halogenating reagent is used in an amount of about 1 to about 30 equivalents, preferably about 1 to about 10 equivalents per equivalent of the allenyl β-lactam compound of the formula (1), although varies widely and is suitably selected depending on the kind of the halogenating reagent, the amount of the allenyl β-lactam compound of the formula (1), kind of the copper salt, and reaction conditions. When required, it is possible to add the halogenating reagent until the allenyl β-lactam compound of the formula (1) is consumed.

The reaction is conducted in a suitable solvent. Examples of solvents useful in the reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran and dioxane, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclooctane, amides such as dimethylformamide, dimethylacetamide and N-methyl-2-pyrrolidone or cyclic amide, dimethylsulfoxide, etc. These solvents are used singly or in admixture of at least two of them. The solvent is used in an amount of about 10 to about 200 liters, preferably about 20 to about 100 liters, per kilogram of the compound of the formula (1), although varies widely and is suitably selected depending on the kind of the solvent, the amount of the allenyl β-lactam compound of the formula (1), kind and amount of the copper salt and the halogenating reagent, and reaction conditions.

The reaction is conducted usually at about −78° C. to about +60° C., preferably about −20° C. to about +30° C. The reaction can be conducted, as required, in a sealed vessel, or at an atmosphere of an inert gas such as nitrogen gas.

Further, in the present invention, the desired compound can be obtained in much improved yield by introducing oxygen or air into the reaction system. Moreover, it is possible to recycle the catalyst by introducing oxygen or air into the reaction system. Namely, the 3-halogenated cephem derivative can be prepared quantitatively, by supplying the starting material, halogenating reagent and oxygen or air continuously or batchwise, and then supplying a catalytic amount of the copper salt to the reaction system only at the commencement of the reaction. The oxygen or air can be introduced into the reaction system by a usual method. For example, the reaction is conducted at an atmosphere of oxygen or air, the reaction is conducted under bubbling of oxygen or air, etc. In the present invention, sulfinic acid is oxidized by cupric salt. However, in case of using cuprous salt, the salt is easily converted to cupric salt only by conducting the reaction at an atmosphere of oxygen or air, thus the desired reaction proceeds. Accordingly, the introduction of oxygen or air into the reaction system is especially effective in case of using cuprous salt.

The resulting 3-halogenated cephem derivative of the formula (2) can be isolated by the usual purification methods such as extraction, distillation and chromatography.

BEST MODE OF CARRYING OUT THE INVENTION

The present invention will be described below in detail with reference to examples.

EXAMPLE 1

A 130 mg quantity of compound (1a) ($R^1$=PhCH$_2$CONH, $R^2$=H, $R^3$=CH$_2$C$_6$H$_4$OCH$_3$-p, $R^4$=Ph), 8 mg (0.2 equivalent) of anhydrous copper (II) chloride as a copper salt, and 196 mg (20 equivalents) of anhydrous lithium chloride as a halogenating reagent were weighed out, placed into a 10-ml egg-plant type flask and dissolved in 10 ml of N-methyl-2-pyrrolidone serving as a solvent. To the solution was bubbled oxygen (oxidation gas), followed by stirring at room temperature for 6 hours. The reaction mixture was poured into 1N-HCl and extracted with ethyl acetate. The extract was washed with water twice and then with aqueous solution of saturated sodium chloride once and thereafter dried over anhydrous sodium sulfate. The resulting extract was concentrated in vacuo to remove the solvent, and the residue was subsequently purified by silica gel column chromatography to afford compound (2a) (99 mg, 90%) $^1$H-NMR (CDCl$_3$)d; 3.42(d, J=17.8 Hz, 1H), 3.72(d, J=17.8 Hz, 1H), 3.58(d, J=16.4 Hz, 1H), 3.64(d, J=16.4 Hz, 1H), 3.79(s, 3H), 4.96(d, J=5.1 Hz), 5.21(s, 2H), 5.79(dd, J=5.1, 9.2 Hz, 1H), 6.39(d, J=9.2 Hz, 1H), 6.82–7.40(m, 9H)

EXAMPLE 2

The same reaction as in Example 1 was conducted using, as a starting material, 150 mg of compound (1b) ($R^1$=PhCH$_2$CONH, $R^2$=H, $R^3$=CHPh$_2$, $R^4$=Ph) to obtain the compound (2b) (114 mg, 92%).
$^1$-NMR (CDCl$_3$)d; 3.43(d, J=18.9 Hz, 1H), 3.58(d, J=16.2 Hz, 1H), 3.65(d, J=16.2 Hz, 1H), 3.73(d, J=18.9 Hz, 1H), 4.99(d, 18.9 Hz), 5.83(dd, J=4.8, 9.3 Hz, 1H), 6.24(d, J=9.3 Hz, 1H), 6.97(s, 1H), 7.21–7.42(m, 15H)

EXAMPLES 3 to 7

The same reaction as in Example 1 was conducted using the halogenating reagent shown below to obtain the compound (2a). The yield is also given.

| Example | halogenating reagent | amount (mg) | yield (%) |
|---|---|---|---|
| 3 | calcium chloride | 499 | 93 |
| 4 | tetraethylammonium chloride | 745 | 85 |
| 5 | cerium chloride | 757 | 80 |
| 6 | magnesium chloride | 428 | 85 |
| 7 | tetrabutylammonium chloride | 1250 | 50 |

EXAMPLES 8 to 12

The same reaction as in Example 1 was conducted using the copper salt shown below to obtain the compound (2a). The yield is also given.

| Example | copper salt | yield (%) |
|---|---|---|
| 8 | CuCl | 92 |
| 9 | CuCl$_2$ · 2H$_2$O | 90 |
| 10 | CuSO$_4$ · 5H$_2$O | 85 |
| 11 | Cu(ClO$_4$)$_2$ · 6H$_2$O | 82 |
| 12 | Copper acetylacetonate | 76 |

EXAMPLES 13 to 16

The same reaction as in Example 1 was conducted using the copper salt shown below in an amount also shown below to obtain the compound (2a). The yield is also given.

| Example | copper salt | amount (eq.) | yield (%) |
|---|---|---|---|
| 13 | CuCl$_2$ · 2H$_2$O | 0.1 | 91 |
| 14 | CuCl$_2$ · 2H$_2$O | 0.4 | 89 |
| 15 | CuCl$_2$ · 2H$_2$O | 1.0 | 85 |
| 16 | CuCl | 1.0 | 86 |

EXAMPLES 17 to 21

The same reaction as in Example 1 was conducted using the oxidation gas and its pressure shown below to obtain the compound (2a). The yield is also given.

| Example | oxidation gas | pressure (atm) | yield (%) |
|---|---|---|---|
| 17 | oxygen | 1 | 90 |
| 18 | oxygen | 2.5 | 87 |
| 19 | oxygen | 5 | 85 |
| 20 | oxygen | 8 | 85 |
| 21 | air | 5 | 80 |

EXAMPLES 22 to 24

The same reaction as in Example 1 was conducted the solvent shown below to obtain the compound (2a). The yield is also given.

| Example | solvent | yield (%) |
|---|---|---|
| 22 | dimethylformamide | 80 |
| 23 | dimethylacetamide | 79 |
| 24 | tetrahydrofuran | 70 |

EXAMPLE 25

The same reaction as in Example 1 was conducted using 150 mg of compound (1a) as a starting material and 44 mg (1.2 equivalents) of copper (II) chlorides.2H$_2$O as an copper salt in a stream of argon to obtain 109 mg (89% yield) of compound (2a).

REFERENCE EXAMPLE 1

The compound (2) of the present invention can be converted to cefaclor widely used as an oral preparation by the method described in literatures. Namely, compound (2) is subjected to deprotection at 7-position by using phosphorus pentachloride and pyridine (JP-A-3356/1986) to convert to compound (3), and an amide side chain is introduced at 7-position. Thereafter, compound (3) is subjected to derrotection at 4-ester position to obtain cefaclor (JP-A-39313/

1986). The reaction equation is shown below.

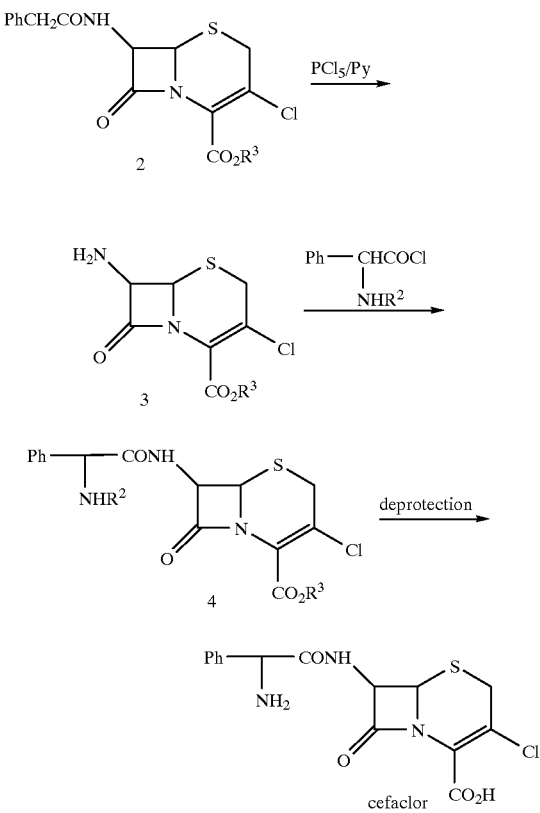

INDUSTRIAL APPLICABILITY

Accoding to the present invention, it is possible to provide the desired 3-halogenated cephem derivative in a high yield with a high purity by a safe and simplified procedure without using a starting material which is difficult to prepare.

We claim:

1. A process for preparing a 3-halogenated cephem derivative represented by the formula (2), characterized by causing a halogenating reagent to act on an allenyl β-lactam compound represented by the formula (1) in the presence of a cupric salt to obtain the 3-halogenated cephem derivative

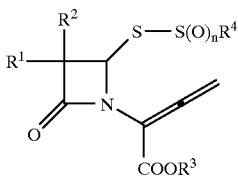

(1)

wherein
$R^1$ is a hydrogen atom, amino or protected amino, $R^2$ is a hydrogen atom, halogen atom, lower alkoxyl, lower acyl, lower alkyl, lower alkyl having at least one selected from hydroxyl and protected hydroxyl as a substituent, hydroxyl or protected hydroxyl, $R^3$ is a hydrogen atom or carboxylic acid protecting group, $R^4$ is an aromatic compound residue which may have a substituent or nitrogen-containing aromatic heterocyclic compound residue which may have a substituent, and n is 0 to 2

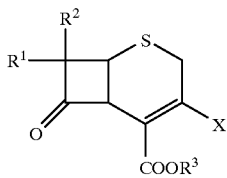

(2)

wherein
$R^1$, $R^2$ and $R^3$ are as defined above, X is a halogen atom.

2. A process for preparing a 3-halogenated cephem derivative represented by the formula (2), characterized by causing a halogenating reagent to act on an allenyl β-lactam compound represented by the formula (1) in the presence of a cuprous salt with introducing oxygen or air into a reaction system to obtain the 3-halogenated cephem derivative.

3. A process for preparing a 3-halogenated cephem derivative as defined in claim 1 wherein the halogenating reagent is a compound of the formula (M)mX or $(R^6)(R^7)(R^8)(R^9)$ N X wherein m is an integer of 1 to 3, M is alkali metal, alkaline earth metal, aluminum or trialkylsilyl, $R^6$ to $R^9$ are the same or different and are hydrogen atom, alkyl, aryl or aralkyl.

4. A process for preparing a 3-halogenated cephem derivative as defined in claim 2 wherein the halogenating reagent is a compound of the formula (M)mX or $(R^6)(R^7)(R^8)(R^9)$ N X wherein m is an integer of 1 to 3, M is alkali metal, alkaline earth metal, aluminum or trialkylsilyl, $R^1$ to $R^9$ are the same or different and are hydrogen atom, alkyl, aryl or aralkyl.

5. A process as defined in claim 1 wherein oxygen or air is introduced into a reaction system.

6. A process for preparing a 3-halogenated cephem derivative as defined in claim 1 wherein the yield of the derivative is at least 50% by weight.

7. A process for preparing a 3-halogenated cephem derivative as defined in claim 2 wherein the yield of the derivative is at least 50% by weight.

8. A process for preparing a 3-halogenated cephem derivative as defined in claim 3 wherein the yield of the derivative is at least 50% by weight.

9. A process for preparing a 3-halogenated cephem derivative as defined in claim 4 wherein the yield of the derivative is at least 50% by weight.

10. A process for preparing a 3-halogenated cephem derivative as defined in claim 5 wherein the yield of the derivative is at least 50% by weight.

* * * * *